United States Patent [19]

Budde

[11] Patent Number: 4,457,300
[45] Date of Patent: Jul. 3, 1984

[54] SURGICAL RETRACTOR

[75] Inventor: Richard B. Budde, Cincinnati, Ohio

[73] Assignee: Ohio Medical Instrument Co., Inc., Cincinnati, Ohio

[21] Appl. No.: 385,483

[22] Filed: Jun. 7, 1982

[51] Int. Cl.³ .............................................. A61B 17/02
[52] U.S. Cl. .................................. 128/20; 128/303.19
[58] Field of Search ...................... 128/20, 303.19, 341, 128/791

[56] References Cited

U.S. PATENT DOCUMENTS

| | | | |
|---|---|---|---|
| 1,460,697 | 7/1923 | Berdlin | 128/20 |
| 1,839,726 | 1/1932 | Arnold | 128/20 |
| 2,549,836 | 4/1951 | McIntyre et al. | 128/303.19 |
| 2,586,488 | 2/1952 | Smith . | |
| 2,594,086 | 4/1952 | Smith . | |
| 2,670,731 | 3/1954 | Zoll et al. . | |
| 3,046,072 | 7/1962 | Douglas et al. | 128/20 |
| 3,522,799 | 8/1970 | Gauthier | 128/20 |
| 3,638,973 | 2/1972 | Poletti | 128/20 |
| 3,766,910 | 10/1973 | Lake . | |
| 3,810,462 | 5/1974 | Szpur . | |
| 3,858,578 | 1/1975 | Milo | 128/20 |
| 3,998,217 | 12/1976 | Trumbull et al. . | |
| 4,010,741 | 3/1977 | Gauthier . | |
| 4,099,521 | 7/1978 | Nestor et al. . | |
| 4,143,652 | 3/1979 | Meier et al. . | |
| 4,254,763 | 3/1981 | McCready et al. . | |

FOREIGN PATENT DOCUMENTS

| | | | |
|---|---|---|---|
| 8100965 | 12/1981 | Fed. Rep. of Germany | 128/20 |
| 446439 | 3/1949 | Italy | 128/20 |

OTHER PUBLICATIONS

*Instruments for Surgery & Microsurgery*, Holco Catalogue Leyla Brain Retractor, 1971.

Primary Examiner—Edward M. Coven
Assistant Examiner—Max F. Hindenburg

[57] ABSTRACT

A surgical retractor is provided for retaining tissue, membrane and organs in a retracted position from an incision during a surgical procedure which includes a tiltable ring having an outwardly extending channel to receive arm support means having a projection captured within and movable along the channel. Retractor arms are mounted to the arm support means such that they pass below the ring and extend inwardly toward the incision so as to not obstruct the surgeon's line of sight or movement of the hands along the ring.

6 Claims, 5 Drawing Figures

SURGICAL RETRACTOR

FIELD OF THE INVENTION

This invention relates generally to the field of surgical appliances, and more particularly, to a device for mounting and positioning flexible arms for retracting membranes, particularly of the brain, during surgical operations.

BACKGROUND OF THE INVENTION

Surgical retractors for holding tissues, at the edge of a surgical incision or wound, away from the field of an operation have been in use for several decades. Early designs such as shown, for example, in Smith U.S. Pat. Nos. 2,586,488 and 2,594,086 provide an annular or ring-like support which is laterally and vertically adjustable along a mounting assembly adapted to be secured to an operating table. Disposed at intervals around the annular support are a plurality of slide arms having bendable retracting elements at their inwardly extending ends which contact the skin, viscera or organs in the field of operation and retain them out of the surgeon's way while the operation is being conducted. Relatively awkward and cumbersome securing means are provided to attach the slide arms in place on the annular support. Similar devices have been utilized for performing operations on the brain such as shown, for example, in Lake U.S. Pat. No. 3,766,910. Such retractors extend inwardly from the ring's top surface, and are clamped or otherwise secured along the top surface of the ring.

The so-called Greenberg retractor and handrest assembly is currently one of the most popular retraction devices used by neurosurgeons. The Greenberg assembly consists of a single or multiple support bars which are clamped together end-to-end beginning with one support bar attached to the skull clamp used to hold the patient's cranium securely in place during an operation. One or more retractor support arms having flexible blades at their inwardly extending ends are movably mounted to the support bars and are slidable therealong for positioning the support arms and flexible blades at desired locations to provide suitable retraction at the incision. Care must be taken in adjusting the position of the clamps because they may be loosened to the point where they will fall off the support bars. Additional retractor support bars and support arms may be added to provide further retraction capability as the operation progresses.

The problem of difficult and inconvenient adjustment of the position of the retractor arms is common to the Greenberg system and many of the other prior art devices. In some designs, further assembly of parts during the operation is required to obtain the desired number and positioning of retractor arms. Even those who have had experience in using such systems may find it difficult to quickly perform the necessary assembly as the operation progresses. In addition, the large number and orientation of elements which make up a system such as the Greenberg assembly tends to obstruct the surgeon's view and get in the way as the hands are shifted from one position to another during the operation.

It has therefore been an object of this invention to provide a surgical retractor which is simple in construction and needs no further assembly once the operation is in progress.

It is another object of this invention to provide a surgical retractor in which flexible retractor arms are slidably and removably captured within a channel formed in a ring support, for rapid and easy adjustment of the position of such retractor arms during an operation.

It is a further object of this invention to provide a surgical retractor having a ring support defining the field of the operation which support serves the dual purpose of positioning arms for retracting tissue from the incision and also acting as a stabilizing handrest for the surgeon.

DESCRIPTION OF THE DRAWINGS

The structure, operation and advantages of this invention will become apparent upon consideration of the following discussion taken in conjunction with the accompanying drawings wherein:

FIG. 2 is an exploded perspective view of the device of the invention;

FIG. 3 is a partial cross-sectional view taken generally along line 3—3 of FIG. 2 showing the ball and socket connection between the ring and support assembly;

FIG. 4 is a partial cross-sectional view taken generally along line 4—4 of FIG. 2 in which the vertical adjustment means of the support assembly is illustrated; and FIG. 5 is a partial cross-sectional view taken generally along line 5—5 of FIG. 1 in which the engagement between the arm support means and ring herein is shown.

DESCRIPTION OF THE INVENTION

Figure 1:
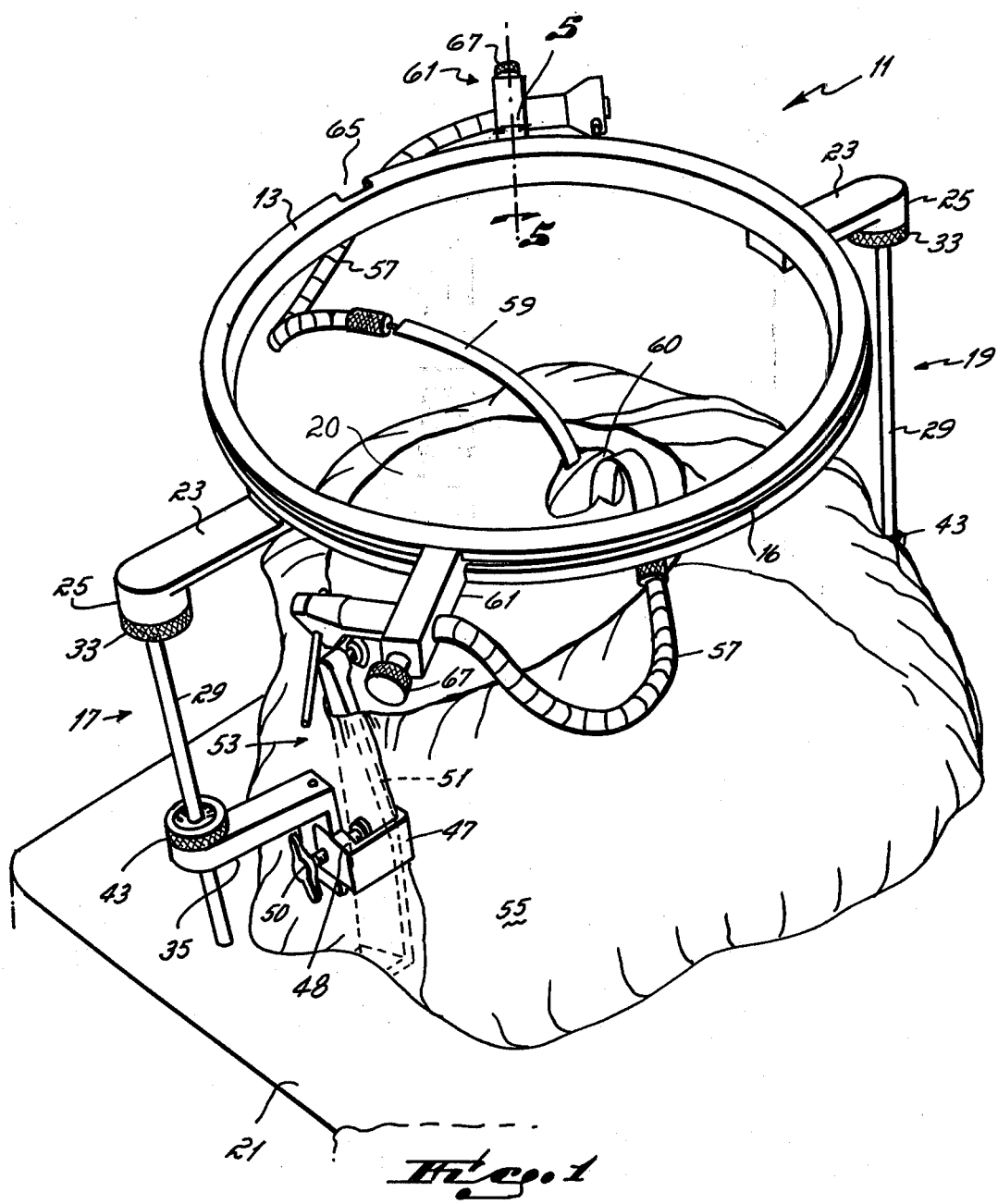
FIG. 1 is an overall perspective view of a preferred embodiment of the surgical retractor of this invention, illustrating its use in a surgical proceeding involving opening the skull.
Figures 2, 3, 4, 5:
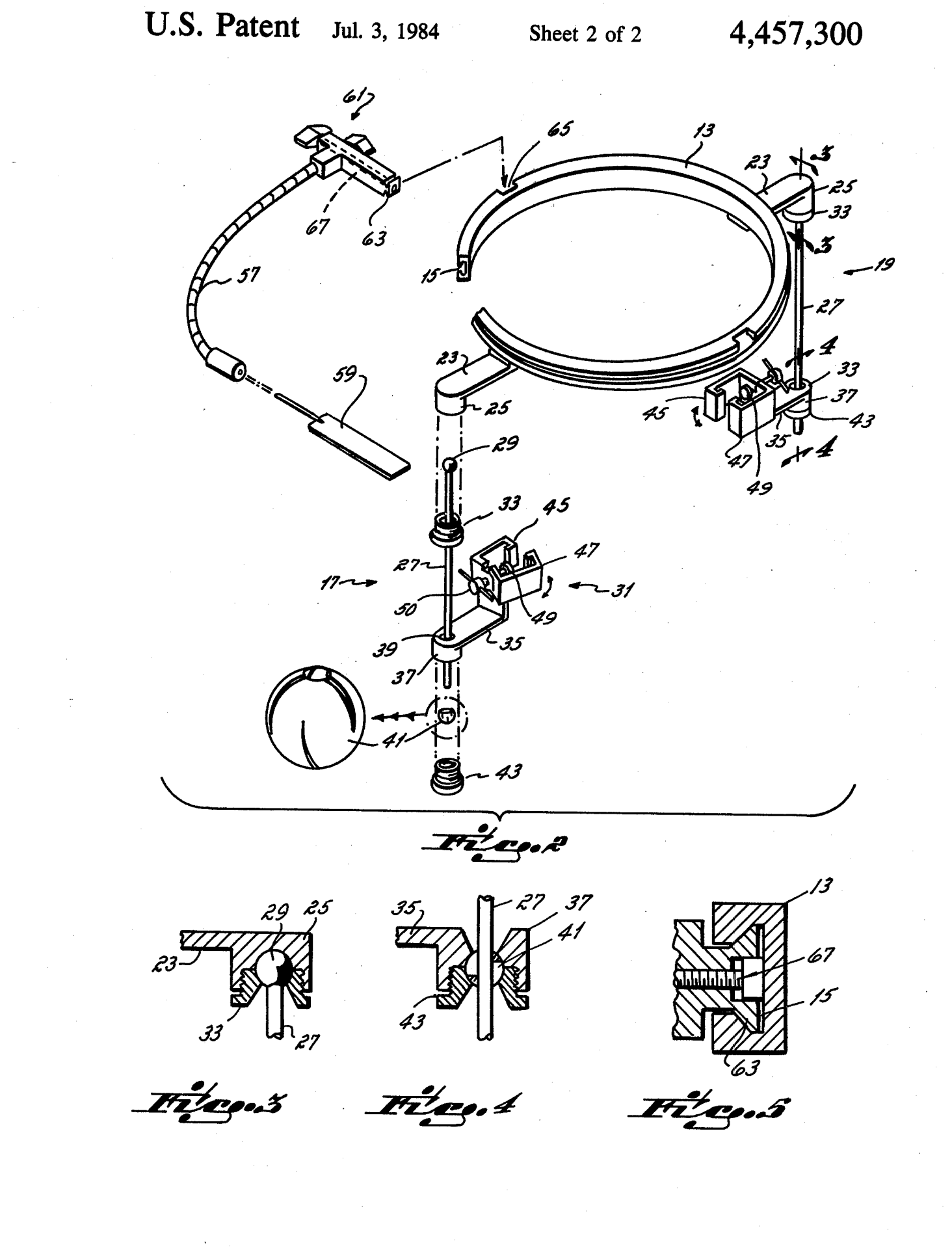

Referring now to the drawings and in particular to FIGS. 1 and 2, the surgical retractor of this invention is designated generally by the reference number 11. The retractor 11 comprises an annulus or ring 13 having a continuous outwardly-opening dove-tail shaped channel 15 formed about its exterior circumference 16. In use, ring 13 is disposed in a desired orientation above the skull of the patient by two upstanding support assemblies 17 and 19, which are approximately 180° apart on ring 13. The support assemblies 17 and 19 are operable to permit ring 13 to be tilted relative to the plane of the operating table 21 and to adjust vertically the ring 13 relative to the patient's head, an upper portion of which is shown at 20, and operating table 21.

Each of the support assemblies 17 and 19 is identical in structure and operation and thus only the support assembly 17, shown in complete detail in FIGS. 1 and 2, is discussed, with like reference numerals applying to support assembly 19. Support assembly 17 includes an upper support arm 23 which is rigidly mounted to the lower surface of ring 13 at one end and extends outwardly, parallel to the plane of the ring. The other end of upper arm 23 is formed with a downwardly extending threaded socket 25 (see FIG. 3). An elongated support rod 27 having a ball 29 fixed at its upper end extends between a table mounting bracket assembly 31 disposed below ring 13, and the socket 25 of upper arm 23. The ball 29 of rod 27 seats as a universal joint within socket 25 of upper arm 23 and is held there by a threaded bushing 33 which is tightened within the threaded socket 25 of arm 23. Ring 13 may be easily tilted about the ball and socket connection thus formed between the rod 27 and upper arm 23, simply by loosening bushing 33 and positioning the ring 13 at any desired angle with respect to horizontal. Once in position, ring 13 is secured in place by tightening bushing 33.

The table mounting bracket assembly 31 comprises a lower arm 35 having a socket 37 in which an opening 39 is formed to receive the rod 27. A split sphere 41 (see FIG. 2) is slipped along rod 27 and seated within the socket 37 of lower arm 35 where it is secured by a second threaded bushing 43 (FIG. 4). Rod 27 is movable upwardly and downwardly relative to the lower arm 35 for positioning ring 13 at the appropriate height relative to the patient's skull. Such adjustment is accomplished by loosening second bushing 43 and allowing the split sphere 41 to move upwardly or downwardly along rod 27 as desired, and then tightening the second bushing 43 when rod 27 is properly positioned. As shown in FIGS. 1 and 2, the socket 37 of lower arm 35 may face upwardly or downwardly relative to the socket 25 and provide the same function.

The lower arm 35 is maintained in a fixed vertical position relative to the operating table 21 by means of a pair of C-shaped clamp arms 45 and 47 which are mounted to the respective ends of the lower arms 35,35 opposite their sockets 37 so that the open portions of the C-shaped arms 45 and 47 face one another. One of the clamp arms 45 or 47 is fixed to a block 48 and the other is pivotally mounted thereto, which block 48 receives a threaded rod 50. The opposite end of blocks 45 and 47 is formed to engage an upstanding rail 51 of a skull clamp 53 which is used to place the patient's head 20 in the proper position on operating table 21 and maintain it there during the operation. The pivotal clamp arm 45 or 47 is swung outwardly so that both clamp arms 45 and 47 engage rail 51, and then the threaded rod 50 is tightened against the rail 51 to urge clamp arms 45 and 47 in the opposite direction for securely mounting lower arms 35,35 to skull clamp 53.

In addition to providing a stable vertical support for ring 13, the clamp arms 45 and 47 help maintain a sterile field during an operation. As shown in FIG. 1, a sterile, surgical cloth 55 is placed over the operating table 21, skull clamp 53 and about the patient's head 20. To hold cloth 55 in place during the operation and avoid contaminating the field of the operation, the cloth 55 is first positioned over the skull clamp 53 and the clamp arms 45 and 47 are then secured to the rails 51 thereof to firmly hold the cloth 55 in place.

As mentioned above, the major problems with existing surgical retractors stem from their relative complexity. In some cases actual assembly of the device must take place during the operation itself. In addition, the hardware utilized to make the prior art devices adjustable and sufficiently stable, can obstruct the surgeon's access to the field of the operation and make difficult even minimal hand motions without interference. In contrast, the placement of ring 13 and any subsequent vertical or angular adjustments which may be necessary during an operation, are readily accomplished as indicated in the discussion above.

The adjustment, positioning and configuration of the retractor arms according to this invention are greatly improved compared to prior art devices. Referring again to FIGS. 1 and 2, one or more flexible retractor arms 57 are provided each having a spatula-like blade 59 mounted at their inwardly extending end. The other end of each retractor arm 57 is mounted to an arm holder 61 formed with a projection or channel interlock 63 which is insertable within the dove-tail channel 15 of ring 13 through one or more slots 65 which extend from an upper or lower surface of ring 13 to the dove-tail channel 15. The arm holders 61 are readily movable to any location along dove-tail channel 15 so that the retractor arms 57 and blades 59 may be positioned at any desired location with respect to the incision 60 in the patient's head. An elongated threaded rod 67 extends through the arm holder 61 and projection 63, and is operable to urge projection 63 into engagement with the angulated surface of the dove-tail channel 15 to secure the retractor arm 57 at any point therealong.

A useful type of flexible member for use in the retractor is one which is comprised of a series of interconnected ball and socket segments through which a cable passes and which can be tightened to exert axial compression on the segment and thereby lock them in a desired curve. Such flexible members are made by Flexbar Machine Corporation and do not comprise the invention.

Unlike prior art means for supporting retractor arms and/or blades, the arm holder 61 may be quickly released. This is done by loosening screw 67 and sliding arm blade 61 in channel 15 from one location to another along the circumference of ring 13, and then resecuring it at such location in a minimal amount of time and with little effort. Since the projection 63 of each arm holder 61 is captured within channel 15, there is no danger of a retractor arm 57 falling from the ring 13, unlike prior art clamping devices.

It is important to note that the arm holders 61 project radially outwardly from ring 13, and the retractor arms 57 extend downwardly from them, outwardly of the ring 13, and then downwardly beneath the ring 13 to the incision 60. This leaves the top surface of ring 13 unobstructed to reduce interference with the surgeon's line of sight to the field of the operation and to enable him to slide his hands over the top surface of ring 13 for support without interference from the retractor arms 57 or other elements of surgical retractor 11. This is in contrast to prior art devices wherein the retractor arms project directly inwardly in the plane of the ring, and wherein they are secured on top of the ring, where they obstruct a smooth ring support surface.

While the invention has been described with reference to a preferred embodiment, it will be understood by those skilled in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the preferred embodiment that is disclosed, but that the invention will include all embodiments falling within the scope of the appended claims.

I claim:

1. A surgical retractor for retaining tissue, membrane, organs and the like in retracted position in an incision during a surgical procedure, comprising:
   a ring having an unobstructed planar upper surface and a continuous, circumferentially outwardly opening channel around its periphery;
   support means connected to said ring for holding it in a desired position over said incision, said support means including ring support arms mounted to said ring below said channel and projecting outwardly of its periphery, and support rods extending downwardly from outer ends of said ring support arms so that the support means does not extend above the ring or into its center;

at least one retractor arm holder having a projection slidably captured within said outwardly opening channel of said ring, said arm holder extending outwardly from said ring and not extending over said upper surface or into the center of said ring, said projection being movable within said channel around said periphery of said ring to position said arm holder at a desired location therealong;

at least one retractor arm having a blade attached thereto, said retractor arm being mounted to said arm holder outwardly of said ring so that it can pass below and inwardly of said ring without extending over said upper surface thereof;

said retractor arm holder being movable around said channel past said support means without interference therefrom, to position said blade relative to said incision; and said retractor presenting a continuous, unobstructed upper surface which provides a rest and guide for stabilizing a surgeon's hand during said surgical procedure.

2. The surgical retractor of claim 1 wherein said channel is formed in a dove-tail shape.

3. The surgical retractor of claim 1 wherein said ring is formed with at least one opening to receive said projection of said arm support means within said channel.

4. The surgical retractor of claim 1 wherein said support means includes a pair of ring support arms oppositely attached to said ring, each of said ring support arms projecting outwardly of said ring and presenting a socket; a pair of support rods each having a ball at the upper end, said balls seating within respective ones of said sockets in said ring support arms thereby forming ball and socket connections for disposing said ring in desired orientation, said support rods extending downwardly through respective sockets formed in a pair of clamp support arms, a split sphere being slidably disposed along each of said support rods and seating within respective sockets of said clamp support arms, said support rods being vertically movable relative to said clamp support arms for vertically positioning said ring at desired elevation, said support rods being securable on the split spheres by bushings.

5. The surgical retractor of claim 4 wherein said ring support arms are secured to a lower surface of said ring, and do not project above or block said channel.

6. The surgical retractor of claim 5 further including a pair of bracket assemblies to secure respective ones of said clamp support arms to a fixed support, each of said bracket assemblies including a pair of clamp means pivotally connected at one end, the other end of said clamp means adapted to be connected to a fixed support on an operating table, and screw means for operating said clamp means to securely engage said fixed support.

* * * * *